United States Patent
Demianovich, II

(10) Patent No.: US 8,699,668 B2
(45) Date of Patent: Apr. 15, 2014

(54) COMPOSITE MATERIAL X-RAY COLLIMATOR AND METHOD OF MANUFACTURING THEREOF

(75) Inventor: Nicholas Demianovich, II, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 472 days.

(21) Appl. No.: 13/093,936

(22) Filed: Apr. 26, 2011

(65) Prior Publication Data

US 2012/0275560 A1    Nov. 1, 2012

(51) Int. Cl.
*G21K 1/02* (2006.01)

(52) U.S. Cl.
USPC ............................ 378/147; 378/16; 378/150

(58) Field of Classification Search
CPC .............. G21K 1/02; G21K 1/04; A61B 6/06
USPC ............................................ 378/16, 147, 150
See application file for complete search history.

(56) References Cited

U.S. PATENT DOCUMENTS

| | | | | |
|---|---|---|---|---|
| 3,921,001 | A * | 11/1975 | Edholm et al. | 378/150 |
| 5,210,925 | A | 5/1993 | Morgulis | |
| 6,556,657 | B1 | 4/2003 | Tybinkowski et al. | |
| 7,108,423 | B2 * | 9/2006 | Schmitt | 378/147 |
| 2007/0211848 | A1 * | 9/2007 | Hoge | 378/19 |
| 2013/0177131 | A1 * | 7/2013 | Teng | 378/4 |

* cited by examiner

*Primary Examiner* — Glen Kao
(74) *Attorney, Agent, or Firm* — Ziolkowski Patent Solutions Group, SC

(57) ABSTRACT

A composite material pre-patient collimator for shaping an x-ray beam in a computed tomography (CT) system is disclosed. The pre-patient collimator includes a base comprised of a first material having a first material density and an insert mechanically coupled to the base and being comprised of a second material, the second material comprising a moldable material having a second material density greater than the first material density and that is sufficient to block high frequency electromagnetic energy. The base comprises a plurality of structural features by which the insert is molded to the base, with the moldable material of the insert forming a connection with the plurality of structural features to mechanically couple the base and the insert.

21 Claims, 5 Drawing Sheets

COMPOSITE MATERIAL X-RAY COLLIMATOR AND METHOD OF MANUFACTURING THEREOF

BACKGROUND OF THE INVENTION

Embodiments of the invention relate generally to computed tomography (CT) imaging and, more particularly, to a composite material pre-patient x-ray collimator for use as part of a CT imaging system and a method of manufacturing thereof.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

In operation, the x-ray source and the detector array are rotated about the gantry within an imaging plane and around the subject. The x-ray source is typically in the form of an x-ray tube that emits x-rays at a focal point, with the x-rays being emitted along diverging linear paths in an x-ray beam. A pre-patient collimator is employed for shaping a cross-section of the x-ray beam and for directing the shaped beam through the patient and toward the detector array. The detector array typically includes a collimator for collimating x-ray beams, a scintillator for converting x-rays to light energy adjacent the collimator, and photodiodes for receiving the light energy from the adjacent scintillator and producing electrical signals therefrom.

In CT imaging systems, the pre-patient collimator used for shaping the x-ray beam has historically been constructed by machining a monolithic piece of tungsten. Forming the pre-patient collimator from tungsten was appropriate because of the material's radiation blocking ability and structural properties. However, it is recognized that tungsten is an expensive material and difficult to machine. Additionally, in newer CT imaging systems that implement larger patient coverage, faster rotation speed, and larger bore sizes, pre-patient collimators formed from tungsten become even less desirable. That is, in such newer CT imaging systems, the centripetal acceleration (i.e., G-load) increases dramatically on the pre-patient collimator due to the increasing radius from the center of rotation, faster rotation speed of the components in the gantry, and larger pre-patient collimator size needed to block the beam in large-coverage systems. The weight and forces imposed on the pre-patient collimator are of concern as it affects dynamic balance of the CT imaging system, as well as agility of motion for the collimator.

Lead has also been recognized as a possible material from which to construct a pre-patient collimator, as lead also exhibits ideal radiation blocking capabilities associated with its material density. Unfortunately, similar to the use of tungsten pre-patient collimators, the high density of lead means that a pre-patient collimator constructed of lead is affected by the G-load increase in newer CT imaging systems. Additionally, lead is recognized as being too soft to be useful as a monolithic material and is not compliant under the Restriction of Hazardous Substances Directive (RoHS).

Therefore, it would be desirable to design a pre-patient collimator that combines the blocking power of a high-density material with the structural support of a lower density substrate material, therefore cutting back on weight and cost of the collimator, while preserving robustness, radiation blocking ability, and RoHS compliance.

BRIEF DESCRIPTION OF THE INVENTION

The invention is a directed method and apparatus for providing a composite material pre-patient x-ray collimator for use as part of a CT imaging system.

According to one aspect of the invention, a pre-patient collimator for shaping an x-ray beam in a computed tomography (CT) system includes a base comprised of a first material, the first material having a first material density, and an insert mechanically coupled to the base and being comprised of a second material, the second material comprising a moldable material having a second material density greater than the first material density and that is sufficient to block high frequency electromagnetic energy. The base comprises a plurality of structural features by which the insert is molded to the base, with the moldable material of the insert forming a connection with the plurality of structural features to mechanically couple the base and the insert.

According to another aspect of the invention, a method of manufacturing a pre-patient collimator for use in a computed tomography (CT) system includes the steps of forming a base from a first material, the base being formed so as to have a plurality of geometrical features thereon and molding a second material onto the base to form an insert, the second material comprising a material having a material density greater than that of the first material and that is sufficient to block high frequency electromagnetic energy. The second material is injection molded onto the base such that the second material forms a mechanical bond with the plurality of geometrical features to secure the insert to the base.

According to yet another aspect of the invention, a computed tomography (CT) system includes a rotatable gantry having an opening to receive an object to be scanned, a high frequency electromagnetic energy projection source configured to project a high frequency electromagnetic energy beam toward the object, and a collimator positioned between the high frequency electromagnetic energy projection source and the object configured to shape the high frequency electromagnetic energy beam, the collimator comprising a pair of blades. The CT system also includes a detector array configured to detect high frequency electromagnetic energy passing through the object and generate a detector output responsive thereto, a data acquisition system (DAS) connected to the detector array and configured to receive the detector output, and an image reconstructor connected to the DAS and configured to reconstruct an image of the object from the detector output received by the DAS. Regarding the collimator, each blade of the collimator further includes a metallic base formed of a first material and comprising a plurality of geometrical features thereon formed therein and an insert mechanically coupled to the base that is formed of a radiation blocking material having a material density greater than a material density of the first material, with the insert being mechanically coupled to the metallic base by way of the plurality of geometrical features, such that the blade is free of adhesives and fasteners for coupling the metallic base and the insert.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
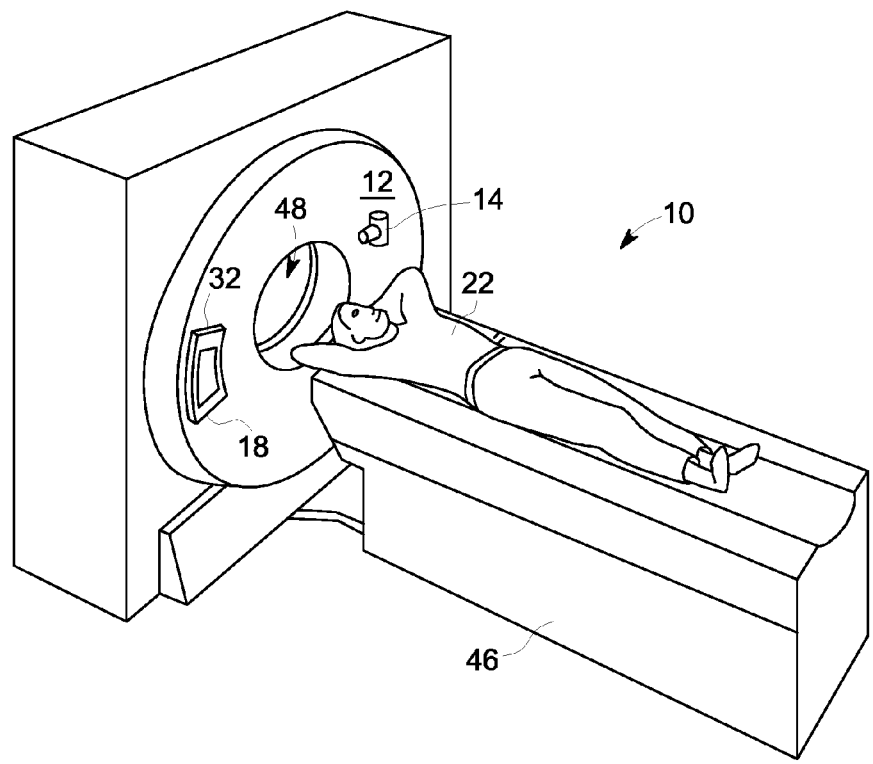
FIG. 1 is a pictorial view of a CT imaging system.
Figure 2:
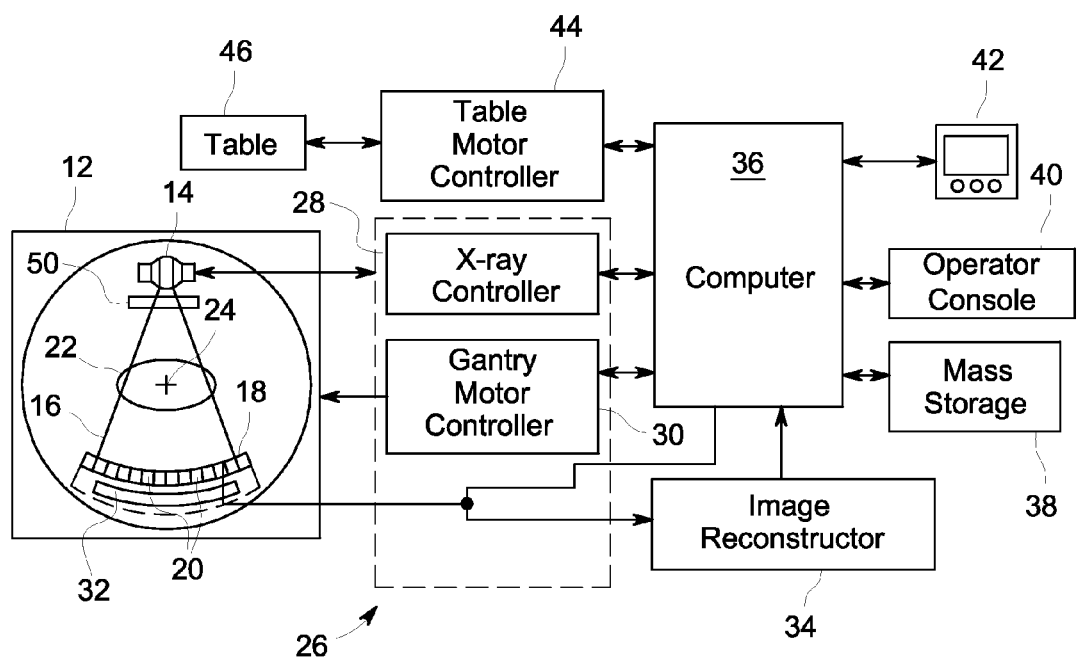
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

As shown in FIG. 2, CT system 10 also includes a pre-patient collimator 50 mounted on gantry 12 and positioned in proximity to x-ray source 14. Collimator 50 is constructed to shape the cross-section of x-ray beam 16 into a shape that matches the shape of detector array 18, such as a rectangular shape, for example. The collimator 50 thus ensures that a patient being scanned is not subjected to an unnecessary dose of x-rays.

Figure 3:
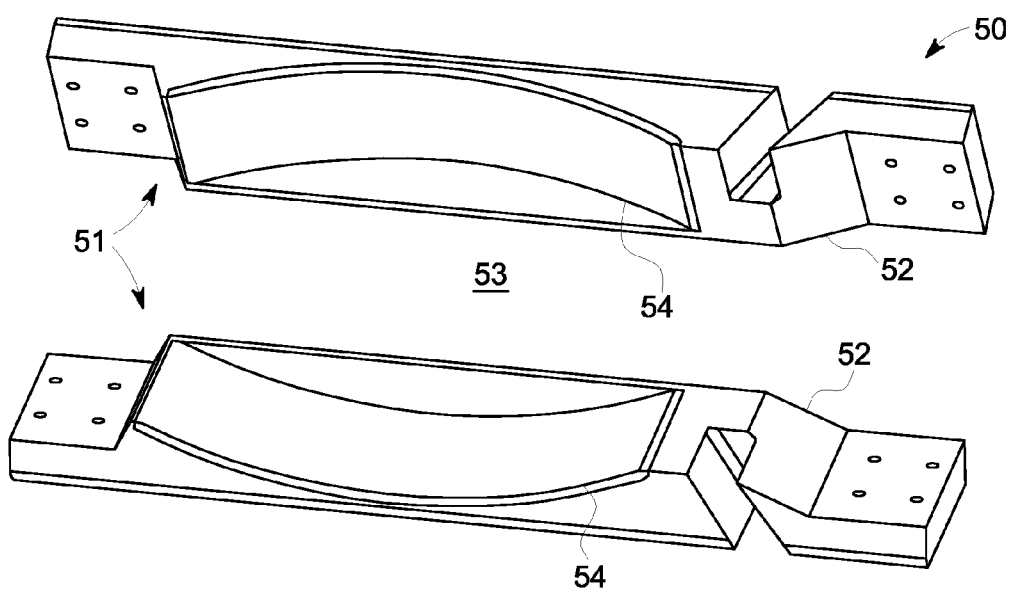
FIG. 3 is a perspective exploded view of a pre-patient collimator assembly for use in the CT imaging system of FIGS. 1 and 2, according to an embodiment of the invention.

Referring now to FIG. 3, an exploded view of the collimator 50 is provided according to one embodiment of the invention. As shown in FIG. 3, collimator 50 is formed of a pair of blades 51 that are adjustable relative to one another so as to vary the size of an aperture 53 formed therebetween for allowing the x-ray beam 16 (FIG. 2) to pass there through. Varying of the size/shape of aperture 53 thus determines the cross-section of x-ray beam 16 and provides for the control and modification of the beam to a desired size/shape, such as to match the shape of detector array 18.

As shown in FIG. 3, each blade 51 is further formed of a base 52 and an insert 54 attached to the base 52. According to embodiments of the invention, each blade 51 of collimator 50 is formed as a composite component, in that the base 52 and the insert 54 are constructed of different materials. More specifically, the base 52 and the insert 54 are formed of materials having different densities. Each blade 51 is formed from a lower density structural material and a high-density radiation blocking material to achieve a resulting composite part that serves to selectively block radiation while also minimizing a weight and cost of the overall collimator 50.

The base(s) 52 of each blade 51 of collimator 50 is constructed to provide structural support to the collimator 50 and allow for securing to gantry 12 of the CT system 10 (FIG. 1), while also being designed to lower the overall weight and cost of the collimator 50. As such, the base 52 is composed of a lower density structural material that is selected based on its ability to preserve the robustness of the collimator 50 without adding undue weight and cost to the collimator 50. As used herein, the term "lower density structural material" refers to a material having a density that is not sufficient to block high frequency electromagnetic energy (e.g., x-ray radiation) from passing there through. According to embodiments of the invention, the base 52 may therefore be formed of aluminum, steel, or another similarly acceptable material, that can be machined to have desired structural characteristics, as set forth in detail below.

The insert 54 of collimator 50 is constructed to provide radiation blocking within the collimator 50. As such, the insert 54 is composed of a high-density radiation blocking material. As used herein, the term "high-density radiation blocking material" refers to a material having a density that is sufficient to block high frequency electromagnetic energy (e.g., x-ray radiation) from passing there through. According to embodiments of the invention, the insert 54 may therefore be formed, in part, of tungsten or another similarly acceptable material, that serves to block and shape the beam of x-rays 16 emitted from x-ray source 14 (FIG. 1), for example. According to an exemplary embodiment, the insert 54 is formed of a moldable high-density radiation blocking material, such as tungsten impregnated plastic, so that the insert 54 can be secured to base 52 by way of mechanical bonding, as set forth in detail below.

According to embodiments of the invention, the composite material blades 51 of collimator 50 are constructed such that base 52 is mechanically bonded to insert 54 without the use of adhesives or mechanical fasteners (e.g., bolts, screws, etc.). According to an exemplary embodiment, insert 54 is formed of a moldable material (e.g., tungsten impregnated plastic) that is molded onto base 52, such as by way of mechanical over-molding or injection molding, to form an inseparable blade 51 in collimator 50. To facilitate the mechanical bonding of the base 52 and the insert 54, the base 52 is constructed to include a plurality of geometrical or structural features thereon that "lock" the insert 54 to the base 52 during a molding of the insert 54 thereto.

Figure 4:
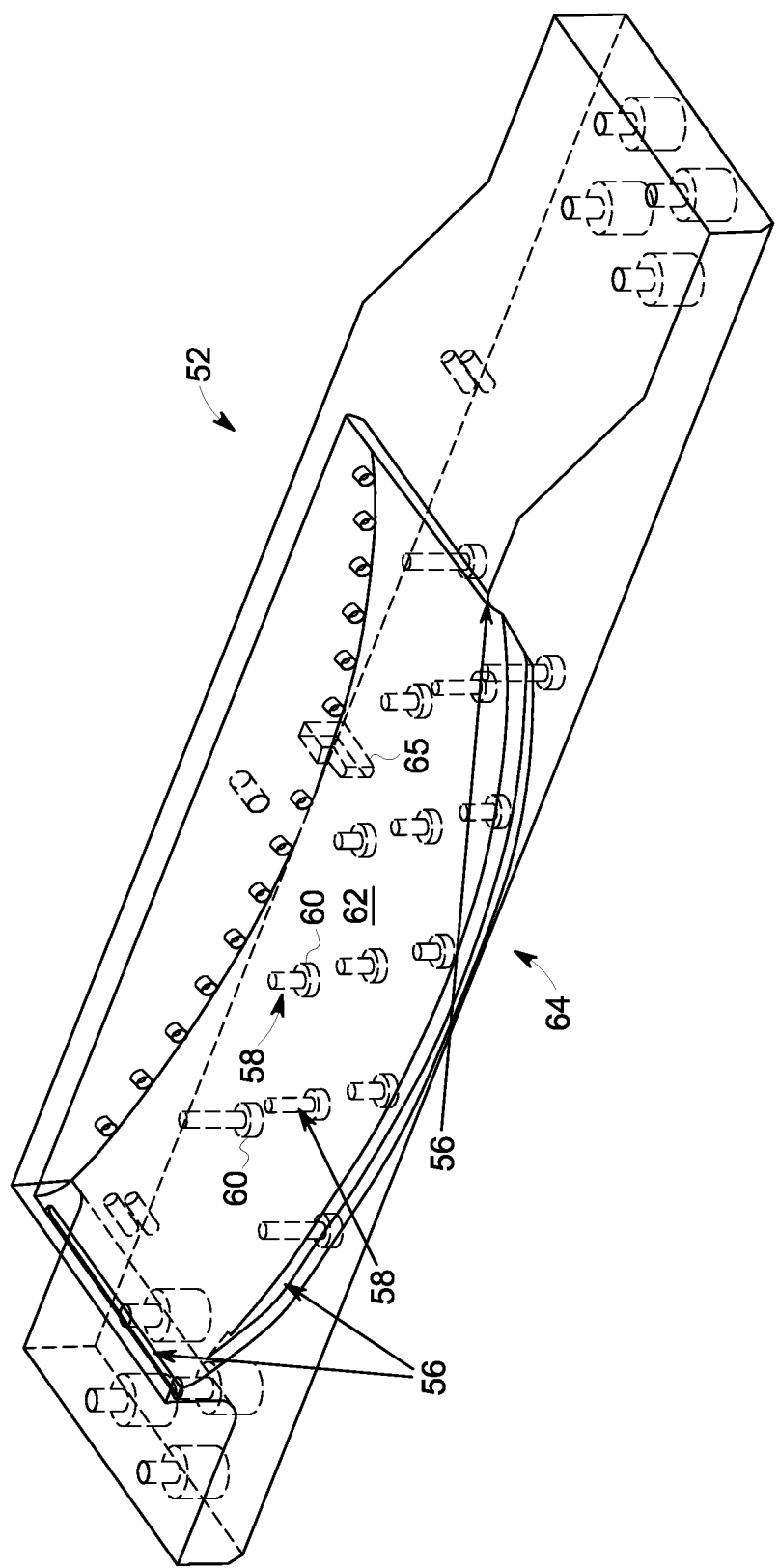
FIG. 4 is a perspective view of a base of the pre-patient collimator assembly of FIG. 3 according to an embodiment of the invention.

Referring now to FIG. 4, a detailed view of base 52 is shown according to an exemplary embodiment of the invention. As shown in FIG. 4, base 52 includes a plurality of geometrical/structural features 56, 58, 60 thereon that provide for a mating of insert 54 thereto when insert 54 is applied/formed via a mechanical over-molding or injection molding process. The base 52 includes a series of undercuts 56 for receiving the insert 54, with the undercuts 56 being formed at opposing ends and sides of an insert placement area 62, for example. The base 52 also includes a series of holes 58 spaced apart in the insert placement area 62, with the holes 58 having counter bores 60 on an exit surface 64 of the base 52 opposite from where insert 54 is placed. According to an exemplary embodiment, undercuts 56 and holes 58 with counter bores 60 are formed in base 52 by way of a machining operation, such as according to standard machining procedures of an aluminum/steel material. According to another embodiment, a notch 65 is cut into the back of the base to serve as a gate for the introducing high-density radiation blocking material of the insert in the molding process.

Figure 5:
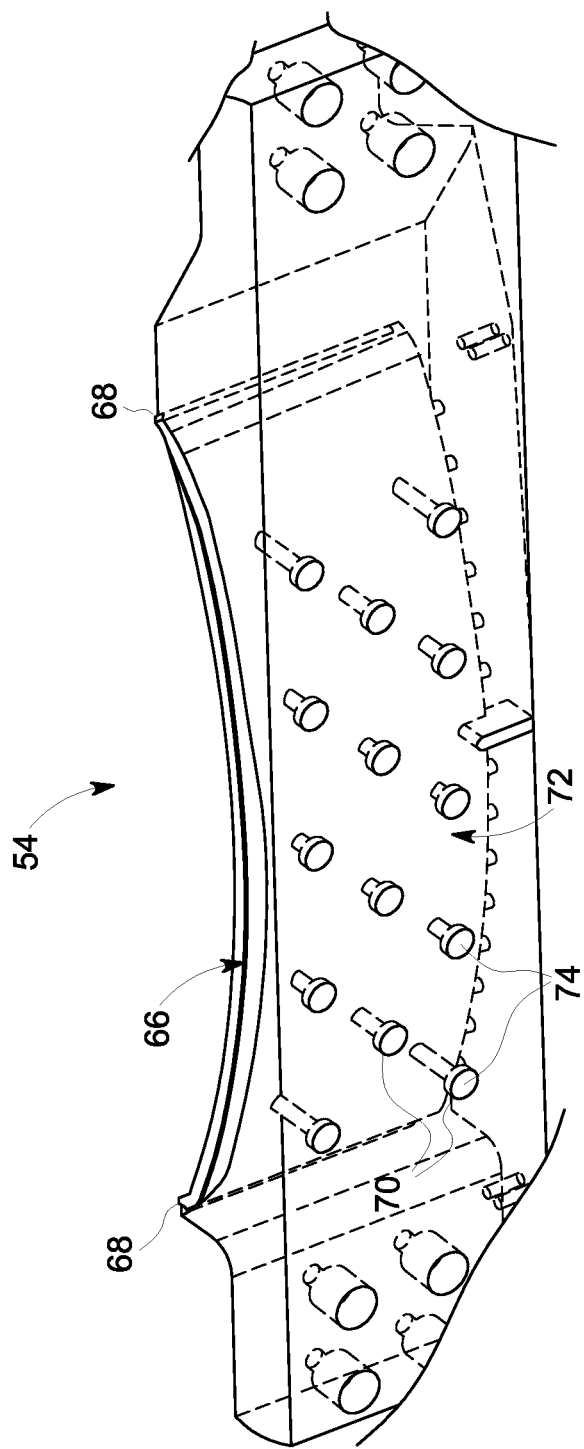
FIG. 5 is a perspective view of an insert of the pre-patient collimator assembly of FIG. 3 according to an embodiment of the invention.

Referring now to FIG. 5, a detailed view of insert 54 is shown according to an exemplary embodiment of the invention. As shown in FIG. 5, insert 54 includes a main face 66 that is generally formed in insert placement area 62 of base 52. According to an exemplary embodiment, face 66 is formed as a curved face that accommodates an asymmetric x-ray beam, optimizes placement from x-ray source 14 (FIG. 1) based on a radius of curvature of the face, and provides full x-ray beam blocking. Alternatively, it is recognized that face 66 could also be formed as a straight (i.e., non-curved) face, according to another embodiment of the invention. Included on insert 54 are lips or protrusions 68 formed at opposing ends of face 66, with the lips/protrusions 68 being formed to mate with undercuts 56 formed on base 52 (FIG. 4). Also included on insert 54 are a series of anchors 70 that extend out from a back surface 72 of face 66 and down through holes 58 formed in base 52. At an end of the anchors 70 distal from face 66, circular flanges 74 are formed that mate with the counter bore 60 of holes 58, to lock the anchor 70 to base 52. As indicated above, insert 54 is formed by way of a mechanical over-molding or injection molding process, such that the lips/protrusions 68 of face 66 and the anchors 70 form a locking mechanical bond with the geometrical features 56, 58, 60 of the base 52, i.e., the undercuts 56 and holes 58 with counter bores 60 formed on/in the base 52.

According to an embodiment of the invention, each blade 51 of the collimator 50 can thus be manufactured by first forming an base 52 from a piece of aluminum or steel, for example, with the aluminum/steel being machined to form an base having a plurality of geometrical features formed thereon. As set forth above, the geometrical features may be in the form of a series of undercuts 56 and holes 58 having counter bores 60 formed therein. Upon machining of the base 52, the insert 54 is molded to the base by way of an over-molding or injection molding process. In molding the insert 54 to the base 52, a number of protrusions 68 are formed on the insert that mate with the undercuts 56 of the base. Additionally, a number of anchors 70 are formed on the insert 54 that mate with the holes 58 and counter bores 60 of the base 52. The molding of the insert 54 to the base 52 forms a mechanical bond there between that secures the insert to the base, without the need for any adhesives and/or fasteners.

Figure 6:
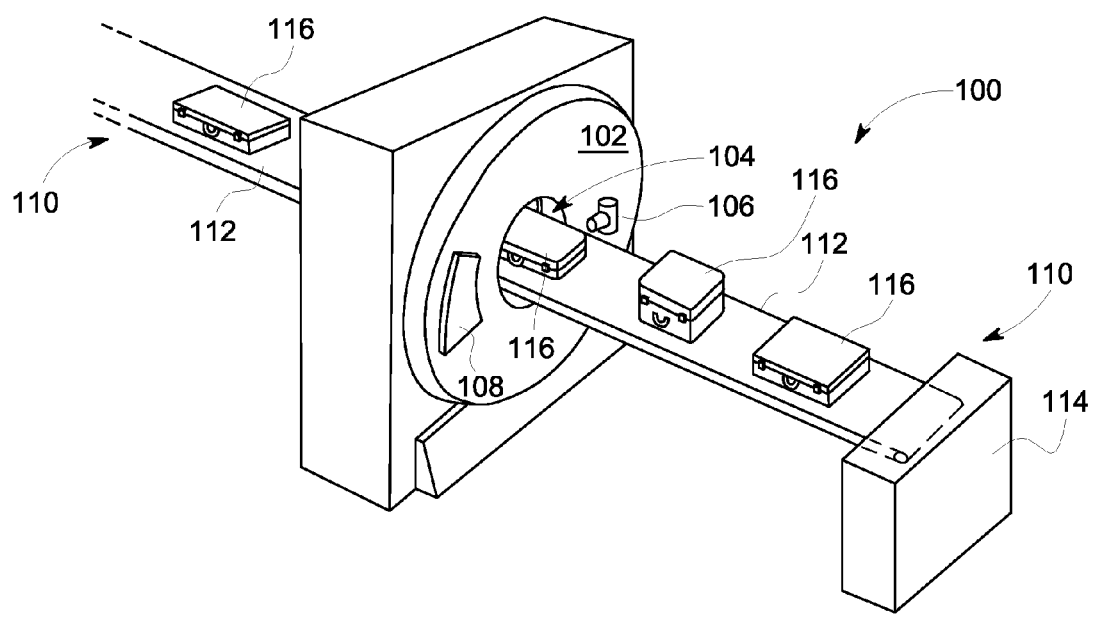
FIG. 6 is a pictorial view of a CT system incorporating a pre-patient collimator assembly for use with a non-invasive package inspection system.

Referring now to FIG. 6, a package/baggage inspection system 100 is shown according to an embodiment of the invention, with the package/baggage inspection system 100 incorporating a pre-patient collimator 50 such as shown in FIG. 3. As shown in FIG. 6, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Beneficially, the composite material pre-patient collimator 50 can be optimized for radiation blocking ability, rigidity, and weight. The reduced weight of the collimator reduces demand on motors and bearings of the CT system since it is lighter. Additionally, the structure of the composite material pre-patient collimator blade, and the mechanical bonding/locking provided thereby, eliminates the need for any separate fasteners or adhesives to be used, thereby also eliminating any leakage points that might be created by the use of such fasteners. Additionally, the molding of the blocking material insert to the base allows for flexibility in geometry and application, and reduces waste and cost by providing a near net shape of the molded insert, such that the resulting insert is more environmentally friendly than using adhesives, for example. Still further, the structure of the composite material pre-patient collimator provides for machining of the assembly that is easier and cheaper than machining a pure tungsten collimator assembly.

Therefore, according to one embodiment of the invention, a pre-patient collimator for shaping an x-ray beam in a computed tomography (CT) system includes a base comprised of a first material, the first material having a first material density, and an insert mechanically coupled to the base and being comprised of a second material, the second material comprising a moldable material having a second material density greater than the first material density and that is sufficient to block high frequency electromagnetic energy. The base comprises a plurality of structural features by which the insert is molded to the base, with the moldable material of the insert forming a connection with the plurality of structural features to mechanically couple the base and the insert.

According to another embodiment of the invention, a method of manufacturing a pre-patient collimator for use in a computed tomography (CT) system includes the steps of forming a base from a first material, the base being formed so as to have a plurality of geometrical features thereon and molding a second material onto the base to form an insert, the second material comprising a material having a material density greater than that of the first material and that is sufficient to block high frequency electromagnetic energy. The second material is injection molded onto the base such that the second material forms a mechanical bond with the plurality of geometrical features to secure the insert to the base.

According to yet another embodiment of the invention, a computed tomography (CT) system includes a rotatable gantry having an opening to receive an object to be scanned, a high frequency electromagnetic energy projection source configured to project a high frequency electromagnetic energy beam toward the object, and a collimator positioned between the high frequency electromagnetic energy projection source and the object configured to shape the high frequency electromagnetic energy beam, the collimator comprising a pair of blades. The CT system also includes a detector array configured to detect high frequency electromagnetic energy passing through the object and generate a detector output responsive thereto, a data acquisition system (DAS) connected to the detector array and configured to receive the detector output, and an image reconstructor connected to the DAS and configured to reconstruct an image of the object from the detector output received by the DAS. Regarding the collimator, each blade of the collimator further includes a metallic base formed of a first material and comprising a plurality of geometrical features thereon formed therein and an insert mechanically coupled to the base that is formed of a radiation blocking material having a material density greater than a material density of the first material, with the insert being mechanically coupled to the metallic base by way of the plurality of geometrical features, such that the blade is free of adhesives and fasteners for coupling the metallic base and the insert.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A pre-patient collimator for shaping an x-ray beam in a computed tomography (CT) system, the pre-patient collimator assembly comprising:
   a base comprised of a first material, the first material having a first material density; and
   an insert mechanically coupled to the base and being comprised of a second material, the second material comprising a moldable material having a second material density greater than the first material density and that is sufficient to block x-ray energy;
   wherein the base comprises a plurality of structural features by which the insert is molded to the base, with the moldable material of the insert forming a connection with the plurality of structural features to mechanically couple the base and the insert.

2. The pre-patient collimator of claim 1 wherein the plurality of structural features of the base comprise:
   a plurality of undercuts formed in the base; and
   a plurality of holes formed through the base, the holes having counter bores formed thereon.

3. The pre-patient collimator of claim 2 wherein the insert comprises:
   a face having protrusions on opposing ends thereof, the protrusions configured to mate with the undercuts formed in the base; and
   a plurality of anchors extending outward from the face, the anchors configured to extend through the holes formed through the base.

4. The pre-patient collimator of claim 3 wherein each of the plurality of anchors further comprises a circular flange positioned at an end of the anchor distal from the face, each circular flange configured to mate with a respective counter bore of the base.

5. The pre-patient collimator of claim 1 wherein the base and the insert form a collimator blade, and wherein the pre-patient collimator comprises a pair of collimator blades having an aperture situated therebetween.

6. The pre-patient collimator of claim 5 wherein a position of at least one of the collimator blades is adjustable, such that a size and shape of the aperture is variable so as to shape an x-ray energy beam as it passes there through.

7. The pre-patient collimator of claim 1 wherein the first material comprises one of aluminum and/or steel.

8. The pre-patient collimator of claim 1 wherein the second material comprises tungsten impregnated plastic.

9. The pre-patient collimator of claim 1 wherein the collimator is free of adhesives or fasteners for mechanically coupling the insert to the base.

10. A method of manufacturing a pre-patient collimator for use in a computed tomography (CT) system, the method comprising:
    forming a base from a first material, the base being formed so as to have a plurality of geometrical features thereon; and
    molding a second material onto the base to form an insert, the second material comprising a material having a material density greater than that of the first material and that is sufficient to block x-ray energy;
    wherein the second material is injection molded onto the base such that the second material forms a mechanical bond with the plurality of geometrical features to secure the insert to the base.

11. The method of claim 10 wherein forming the base comprises:
    providing a piece of metallic stock comprising one of aluminum and/or steel; and
    machining the piece of metallic stock to form the base having the plurality of geometrical features.

12. The method of claim 10 wherein the plurality of geometrical features comprises a series of undercuts and a series of holes with counter bores.

13. The method of claim 12 wherein molding the second material onto the base comprises one of over-molding and injection molding the second material about and through the series of undercuts and series of holes with counter bores, respectively, to form the insert.

14. The method of claim 13 wherein forming the insert further comprises:
    forming an insert face having protrusions on opposing ends thereof, the protrusions configured to mate with the undercuts formed in the base; and
    forming a plurality of anchors extending outward from the insert face, the anchors configured to extend through the holes with counter bores formed through the base.

15. The method of claim 10 further wherein the base and the insert form a collimator blade, and wherein the method further comprises:
providing a pair of collimator blades; and
positioning the pair of collimator blades relative to one another so as to define an aperture therebetween;
wherein a position of at least of the pair of collimator blades is adjustable, such that a size and shape of the aperture is variable so as to shape an x-ray energy beam as it passes there through.

16. The method of claim 10 wherein the second material comprises tungsten impregnated plastic configured to block radiation from passing there through.

17. A computed tomography (CT) system comprising:
a rotatable gantry having an opening to receive an object to be scanned;
an x-ray projection source configured to project an x-ray beam toward the object;
a collimator positioned between the x-ray projection source and the object configured to shape the x-ray beam, the collimator comprising a pair of blades;
a detector array configured to detect x-ray energy passing through the object and generate a detector output responsive thereto;
a data acquisition system (DAS) connected to the detector array and configured to receive the detector output; and
an image reconstructor connected to the DAS and configured to reconstruct an image of the object from the detector output received by the DAS;
wherein each blade of the collimator comprises:
a metallic base formed of a first material and comprising a plurality of geometrical features thereon formed therein; and
an insert mechanically coupled to the base, the insert being formed of a radiation blocking material having a material density greater than a material density of the first material;
wherein the insert is mechanically coupled to the metallic base by way of the plurality of geometrical features, such that the blade is free of adhesives and fasteners for coupling the metallic base and the insert.

18. The CT system of claim 17 wherein the plurality of geometrical features comprises:
a plurality of undercuts formed in the metallic base; and
a plurality of holes with counter bores formed through the metallic base, the plurality of holes formed in an area of the metallic base configured to receive the insert.

19. The CT system of claim 18 wherein the insert comprises:
a face having protrusions on opposing ends thereof, the protrusions configured to mate with the undercuts formed in the metallic base; and
a plurality of anchors extending outward from the face, the anchors configured to extend through the holes with counter bores formed through the metallic base.

20. The CT system of claim 17 wherein the radiation blocking material comprises a moldable tungsten impregnated plastic.

21. The CT system of claim 17 wherein the pair of blades are positioned so as to define an aperture therebetween, and wherein a position of at least one of the blades is adjustable, such that a size and shape of the aperture is variable so as to shape the x-ray beam as it passes there through.

* * * * *